US008128969B2

(12) United States Patent
Nakamoto et al.

(10) Patent No.: US 8,128,969 B2
(45) Date of Patent: Mar. 6, 2012

(54) HYPOGLYCEMIC COMPOSITION CONTAINING ACACIA BARK DERIVATIVE

(75) Inventors: Yusho Nakamoto, Hatsukaichi (JP); Keiko Ono, Hatsukaichi (JP)

(73) Assignee: Mimozax Co., Ltd., Hatsukaichi-shi (JP)

( * ) Notice: Subject to any disclaimer, the term of this patent is extended or adjusted under 35 U.S.C. 154(b) by 132 days.

(21) Appl. No.: 12/376,902

(22) PCT Filed: Aug. 10, 2006

(86) PCT No.: PCT/JP2006/315863
§ 371 (c)(1),
(2), (4) Date: Feb. 9, 2009

(87) PCT Pub. No.: WO2008/018138
PCT Pub. Date: Feb. 14, 2008

(65) Prior Publication Data
US 2010/0166899 A1    Jul. 1, 2010

(51) Int. Cl.
*A01N 65/00* (2009.01)
(52) U.S. Cl. ............................................ 424/725
(58) Field of Classification Search .................. None
See application file for complete search history.

(56) References Cited

U.S. PATENT DOCUMENTS

| 5,629,338 | A | 5/1997 | Okuda et al. |
| 6,290,993 | B1 | 9/2001 | Anderson et al. |
| 6,294,190 | B1 | 9/2001 | Nakahara et al. |
| 7,514,469 | B2 * | 4/2009 | Jia .............................. 514/456 |
| 2003/0180402 | A1 | 9/2003 | Jia et al. |
| 2003/0232099 | A1 | 12/2003 | Pan et al. |
| 2004/0186062 | A1 | 9/2004 | Burnett et al. |
| 2005/0058722 | A1 | 3/2005 | Managoli |
| 2005/0095332 | A1 | 5/2005 | Stanley |
| 2006/0204599 | A1 | 9/2006 | Wheat |
| 2008/0124415 | A1 | 5/2008 | Tanaka et al. |

FOREIGN PATENT DOCUMENTS

| CN | 1753881 A | 3/2008 |
| FR | 2 710 533 A1 | 4/1995 |
| JP | 64-025726 U | 2/1989 |
| JP | 3-287507 A | 12/1991 |
| JP | 6-065074 A | 3/1994 |
| JP | 7138178 A | 5/1995 |
| JP | 7-300422 A | 11/1995 |
| JP | 8-259557 A | 10/1996 |
| JP | 9-291039 A | 11/1997 |
| JP | 10025238 A | 1/1998 |
| JP | 11-005975 A | 1/1999 |
| JP | 11-180888 A | 7/1999 |
| JP | 2000-044472 A | 2/2000 |
| JP | 2000044472 A | 2/2000 |
| JP | 2000-073056 A | 3/2000 |
| JP | 2001-064172 | 3/2001 |
| JP | 2001-098264 A | 4/2001 |
| JP | 2002010753 A | 1/2002 |
| JP | 2002-051736 A | 2/2002 |
| JP | 2002-275076 A | 9/2002 |
| JP | 2002275076 A | 9/2002 |
| JP | 2003-519092 A | 6/2003 |
| JP | 2003-313138 A | 11/2003 |
| JP | 2003-342185 A | 12/2003 |
| JP | 2004-008215 A | 1/2004 |
| JP | 2004024054 A | 1/2004 |
| JP | 2004-051513 A | 2/2004 |
| JP | 2004-075579 A | 3/2004 |
| JP | 2004-091464 A | 3/2004 |
| JP | 2004217559 A | 8/2004 |
| JP | 2004-300117 A | 10/2004 |
| JP | 2004532811 T | 10/2004 |
| JP | 2004323362 A | 11/2004 |
| JP | 02004352639 | * 12/2004 |
| JP | 2004352639 A | 12/2004 |
| JP | 2005-068081 | 3/2005 |
| JP | 2005-521715 A | 7/2005 |
| JP | 2005-239559 A | 9/2005 |
| JP | 2005-529898 A | 10/2005 |
| JP | 2006-232781 A | 9/2006 |
| JP | 2006-232782 A | 9/2006 |
| WO | WO 03/082312 A1 | 10/2003 |
| WO | WO 03-092599 A2 | 11/2003 |
| WO | WO 2005-020932 A2 | 3/2005 |
| WO | WO 2006-003909 A1 | 1/2006 |

OTHER PUBLICATIONS

*Acacia mernsii*, 5 pages, 2010.*
Liu et al., "Antidiabetic effect of Pycnogenol® French maritime pine bark extract in patients with diabetes type II" Life Sciences vol. 75, No. 21, 2004, pp. 2505-2513.
Ohara et al., "Condensed Tannins from *Acacia mearnsii* and Their Biological Activities" Mokuzai Gakkkaishi, vol. 40, No. 12, pp. 1363-1374, 1994 (Original Article).
Ohara, "Juhi Tannin no Kagaku Tokusei to Yoko Kaihatsu" APAST, 2003, vol. 13 No. 1, pp. 7-11.
Takagi et al., "Tyrosinase inhibitory activity of proanthocyanidins from woody plants" J. Wood Science, 2003, vol. 49, No. 5, pp. 461-465. Wassel et al., "Phytochemical Examination and Biological Studies of *Acacia nilotica* L.Willd and *Acacia farnesiana* L. Willd Growing in Egypt" Egyptian Journal of Pharmaceutical Sciences, 1992, vol. 33, No. 1-2, pp. 327-340.
Ohara "Chemical Properties and Application Development of Bark Tannin", APAST, vol. 13, No. 1 (2003.1) pp. 7-11 (and English Translation, pp. 1-10).
African Territories Wattle Industry Fund Limited, Properties, Composition, Reactions and Industrial Applications of Mimosa Extract, Jan. 1980. pp. 2-10.
Botha et al., "Condensed tannins: direct synthesis, structure, and absolute configuration of four biflavonoids from black wattle bark ('mimosa') extract," J Chem Soc, Chem Commun, 1978, vol. 16, pp. 700-702.
Byers, "What can randomized controlled trials tell us about nutrition and cancer prevention?" CA Cancer J Clin, Nov.-Dec. 1999, vol. 49, No. 6, pp. 353-361.
Chang et al., "Antioxidant activity of extracts from *Acacia confusa* bark and heartwood," J Agric Food Chem, Jul. 2001, vol. 49, No. 7, pp. 3420-3424.

(Continued)

*Primary Examiner* — Michael Meller
(74) *Attorney, Agent, or Firm* — Birch, Stewart, Kolasch & Birch, LLP

(57) ABSTRACT

It is intended to provide a composition having an excellent hypoglycemic action without potential for adverse side effects and the like even if taken for a long period of time. The composition is a hypoglycemic composition containing an acacia bark derivative.

12 Claims, No Drawings

OTHER PUBLICATIONS

Cheng et al., "A novel approach to microcalcification detection using fuzzy logic technique," IEEE Trans Med Imaging, Jun. 1998, vol. 17, No. 3, pp. 442-450.

De Oliveira et al., "Antitumor Activity of Condensed Flavanols," An. Acad. Brasil Ciênc vol. 44, pp. 41-44, Academica Brasileira de Ciências (1972).

Duan et al., "Condensed tannins from steamed *Acacia mearnsii* bark,"Holzforschung, May 2005, vol. 59, No. 3, pp. 289-294.

Fragrance Journal, 1995, 23(10), pp. 96-102 (with English language abstract).

Garewal et al., "Clinical experience with the micronucleus assay," J Cell Biochem Suppl, 1993, vol. 52, No. 17F, pp. 206-212.

Granziero et al., "Adoptive immunotherapy prevents prostate cancer in a transgenic animal model," Eur J Immunol, Apr. 1999, vol. 29, No. 4, pp. 1127-1138.

Haridas et al., "Avicins: triterpenoid saponins from *Acacia victoriae* (Bentham) induced apoptosis by mitochondrial perturbation," PNAS, May 8, 2001, vol. 98, No. 10, pp. 5821-5826.

http://www.merck.com/mmhe/sec15/ch180/ch180c.html, downloaded Apr. 14, 2009, "Risk Factors for Cancer," last review/revision Aug. 2008 by Bruce A. Chabner, MD; Elizabeth Chabner Thompson, MD, MPH.

http://www.merckmanuals.com/home/sec15/ch180/ch180a.html?ql=cancer&alt=sh, downloaded Dec. 4, 2010, "Overview of Cancer: Merck Manual Home Edition," last full review/revision Aug. 2008 by Bruce A. Chabner, MD; Elizabeth Chabner Thompson, MD, MPH.

Ishida et al., "Solid sampling technique for direct detection of condensed tannins in bark by matrix-assisted laser desorption/ionization mass spectrometry," Rapid Commun Mass Spectrom, 2005, vol. 19, No. 5, pp. 706-710.

Jacobus et al., Condensed Tannins: Direct Sysnthesis, Structure and Absolute Configuration of Four Biflavonoids from Black, Wattle (*Acacia mearnsii*) Bark, J.C. Chem. Comm. 1978. http://pubs.rsc.org/en/content/articlepdf/1978/c3/c39780000700.

Japanese Office Action issued in Japanese Patent Application No. 2005-132746 on Aug. 2, 2011.

Kronborg O., "Population screening for colorectal cancer, the goals and means," Ann Med, Oct. 1991, vol. 23, No. 4, pp. 373-379.

Ohara et al., "Condensed Tannins from *Acacia mearnssi* and Their biological Activities." Mokuzai Gakkaishi, 1994, vol. 40, No. 12, pp. 1363-1374.

Prakash et al., "Characterisation of Tannin from Indian Wattle (*Acacia mearnsii*) Bark," Indian Journal of Forestry, 1991, vol. 14, No. 4, pp. 299-302.

Properties, Composition, Reactions and Industrial Applications of Mimosa Extract, African Territories Wattle Industry Fund Limited, Jan. 1980, London, England.

Roux, "The Biogenesis of Bark and Heartwood Tannins of Some *Acacia* spp. and Their Taxonomic Significance," South African Journal of Science, 1962, vol. 58, No. 12, pp. 389-392.

Seigler, "Phytochemistry of Acacia-sensu lato," Biochemical Systematics and Ecology, 2003, vol. 31, No. 8, pp. 845-873.

Taguchi et al., "Evaluation of antipruritic effect of apple polyphenols using a new animal model of pruritus." J. Tokyo Med. Univ., Feb. 15, 2002, vol. 60, No. 2, pp. 123-129.

Tomatis, "Environmental cancer risk factors. A review." Acta Oncol, 1988, vol. 27, No. 5, pp. 465-472.

U.S. Office Action issued in U.S. Appl. No. 12/376,905 on Dec. 20, 2010.

U.S. Office Action issued in U.S. Appl. No. 12/376,905 on Jan. 3, 2011.

U.S. Office Action issued in U.S. Appl. No. 12/376,895 on Jan. 6, 2011.

U.S. Office Action issued in U.S. Appl. No. 12/376,895 on May 2, 2011.

U.S. Office Action issued in U.S. Appl. No. 12/376,895 on Nov. 2, 2010.

U.S. Office Action issued in U.S. Appl. No. 12/376,904 on Aug. 31, 2010.

U.S. Office Action issued in U.S. Appl. No. 12/376,904 on Feb. 16, 2011.

U.S. Office Action issued in U.S. Appl. No. 12/376,904 on Jun. 17, 2011.

U.S. Office Action issued in U.S. Appl. No. 12/376,939 on Jan. 10, 2011.

U.S. Office Action issued in U.S. Appl. No. 12/376,939 on Jul. 21, 2011.

U.S. Office Action issued in U.S. Appl. No. 12/376,939 on Oct. 7, 2010.

Japanese Office Action issued in JP 2005-132745 on Sep. 13, 2011, with English translation.

Kaur, "Antimutagenicty of ether and ethyl acetate fractionsn of *Acacia nilotica* in Ames assay", Breast, vol. 12, No. Supplement, (2003) p. s47.

Seigler, D.S., Phytochemistry of Acacia-sensu lato, Biochemical Systematics and Ecology, 2003, vol. 31, No. 8, pp. 845-873.

\* cited by examiner

HYPOGLYCEMIC COMPOSITION CONTAINING ACACIA BARK DERIVATIVE

TECHNICAL FIELD

The present invention relates to a hypoglycemic composition derived from a tree belonging to the genus *Acacia*, and to uses of this hypoglycemic composition as a food, an animal feed material, a medicine and a quasi-drug.

BACKGROUND ART

The number of persons exhibiting diabetes or impaired glucose tolerance which would be diabetes, has increased in recent years due to Westernization of the diet, a lack of exercise resulting from the development of transportation facilities and the like. In particular, diabetes causes complications including diabetic neuropathies such as numbness and pain, cataracts, diabetic retinopathy, arteriosclerosis, diabetic nephropathy or diabetic gangrene, and there are also cases that ultimately lead to death. Accordingly, the treatment thereof can be said to be extremely important.

Although improvement of lifestyle is desired for the prevention or treatment of diabetes, this cannot always be easily achieved.

In addition, although the treatment for diabetes involves methods for regulating the level of insulin in the blood by an insulin injection or an oral administration of hypoglycemic agents, these methods are accompanied by adverse side effects, while a diet therapy and an exercise therapy have the problems of being difficult for a patient to comply with them.

Amidst these circumstances, attempts have been made to prevent or treat diabetes and hyperglycemia by using natural ingredients which have a wide range of actions and no potential for adverse side effects and the like even if taken for a long period. For example, Patent Document 1 describes a therapeutic and preventive agent for hyperglycemia containing an extract of a plant belonging to the genus *Bidens*, Patent Document 2 describes a composition for improving hyperglycemia having as an active ingredient a dried acetic acid fermented product of the Amaranthus seed, Patent Document 3 describes a preventive and/or therapeutic agent for a diabetic disease containing as an active ingredient *Sargassum horneri* or a treated product thereof, Patent Document 4 describes a fucoidan-based health food which suppresses hyperglycemia and maintains blood sugar at a low level, and Patent Document 5 describes a food for persons with hyperglycemia containing olive leaves or an extract thereof.

On the other hand, with respect to *acacia, acacia* honey is known, and tannin which is extracted from bark thereof is known to be able to be used as a tanning agent or a wood adhesive, while more recently, extracts of genus *Acacia* have been disclosed to have selective inhibitory effects on COX-2 (Patent Document 6), and bark of genus *Acacia* has been disclosed to have active oxygen eliminating effects (Patent Document 7) and skin whitening effects due to the effect of inhibiting tyrosinase activity (Patent Document 8). However, *acacia* bark and polyphenols derived from *acacia* bark have heretofore not been known to have a hypoglycemic action.

[Patent Document 1] JP2004-323362A
[Patent Document 2] JP7-138178A
[Patent Document 3] JP2004-217559A
[Patent Document 4] JP2004-24054A
[Patent Document 5] JP2002-10753A
[Patent Document 6] JP2004-532811A
[Patent Document 7] JP2004-352639A
[Patent Document 8] JP10-025238A

DISCLOSURE OF THE INVENTION

Problems to be Solved by the Invention

An object of the present invention is to provide a composition having an excellent hypoglycemic action without potential for adverse side effects and the like even if taken for a long period of time.

Means for Solving the Problems

As a result of conducting extensive studies to solve the above problems, the inventors of the present invention found that an acacia bark derivative has an action of lowering blood sugar levels to be useful for the prevention or treatment of a hyperglycemic disease such as diabetes, thereby leading to the completion of the present invention.

Namely, the present invention relates to a hypoglycemic composition containing an *acacia* bark derivative(s).

In addition, the present invention also relates to a method for preventing or treating a hyperglycemic disease such as diabetes using an *acacia* bark derivative(s).

Moreover, the present invention relates to a method for using an *acacia* bark derivative(s) for producing a composition for preventing or treating a hyperglycemic disease such as diabetes.

Effects of the Invention

According to the present invention, a composition having a hypoglycemic action can be provided.

Moreover, according to the present invention, a composition is provided which is safe and has less potential for adverse side effects and the like even if taken for a long period of time.

BEST MODE FOR CARRYING OUT THE INVENTION

There are no particular limitations on the *acacia* bark derivative able to be used in the present invention provided that it is obtained by using as a raw material bark of a tree belonging to the genus *Acacia* (the tree is referred to as "*acacia*" or "genus *Acacia*" hereinafter), examples of which derivatives include a strip and a powder of *acacia* bark, and a suspension thereof, an extract such as a liquid extract, a concentrated liquid extract and a powdered extract of *acacia* bark, and a purified product obtained by purifying these extracts. The extract of *acacia* bark and particularly *acacia* bark polyphenols are preferable for production of excellent hypoglycemic activity.

In the present invention, only a single form of these *acacia* bark derivatives may be used, or alternatively two or more forms thereof may be used in combination.

Although there are no particular limitations on *acacia* able to be used in the present invention so long as it is a tree belonging to the genus *Acacia*, with respect to obtaining an *acacia* bark derivative having an excellent hypoglycemic action, bark of the genus *Acacia* selected from the group consisting of scientific name: *Acacia mearnsii* De Wild. (generic name: black wattle), scientific name: *Acacia mangium* Willd. (generic name: *acacia* mangium), scientific name: *Acacia dealbata* Link, scientific name: *Acacia decurrens* Willd. and scientific name: *Acacia pycnantha* Benth. are preferable, while *Acacia mearnsii* De Wild. and *Acacia mangium* Willd. are particularly preferable.

In the present invention, only a single form of these *acacia* bark may be used, or alternatively two or more forms thereof may be used in combination.

The aforementioned *acacia* bark can normally be obtained by cutting down an *acacia* tree, pealing off only bark and then drying the bark more preferably by sun-drying.

Bark of *acacia* is comprised of an outer bark and a somewhat fibrous inner bark, and when dried to a moisture content of about 20% or less, can be easily finely pulverized with a size reduction mill such as a hammer mill. In the present invention, both the outer bark and inner bark of the genus *Acacia* may be used together or either one may be used alone as the *acacia* bark.

The aforementioned strip of *acacia* bark can be obtained in accordance with commonly used methods by pulverizing the *acacia* bark to a suitable size.

In addition, although the aforementioned powder of *acacia* bark can be obtained by pulverizing the *acacia* bark into a powder in accordance with commonly used methods, in particular, the particle diameter of the resulting powder is preferably 100 μm or less and particularly preferably 50 to 70 μm. Powder fractionation can be carried out by pulverizing the bark dried to a moisture content of 20% or less to a suitable size such as a particle diameter of about 1.6 mm or less, and then classifying the resulting powder with a vibrating screen or the like to obtain the required powder.

The aforementioned extract of *acacia* bark can be obtained by extraction from the *acacia* bark in accordance with commonly used methods. In order to obtain an extract of *acacia* bark having an excellent hypoglycemic action, it is preferably extracted from the *acacia* bark with an alcohol or a polar solvent.

Ethanol, etc. can be used as the alcohol, and water, etc. can be used as the polar solvent, and these solvents may be used singly or in combination of two or more kinds as necessary. A mixed solvent of water and the alcohol such as ethyl alcohol is particularly preferable for production of an excellent hypoglycemic action.

Moreover, the extraction procedure may be carried out a number of times using the same or different solvents.

In terms of obtaining an extract having an excellent hypoglycemic action, an extract which is obtained from the *acacia* bark by extraction with water or hot water, and then further extraction from the resulting extract with ethanol may be used.

Although the extraction is carried out by adding the solvent to a strip, a powder or the like of the *acacia* bark followed by stirring as necessary, there are no particular limitations on temperature, time or solid-liquid ratio. In the case of using water as the solvent, the extraction may also be carried out with hot water. The resulting liquid extract may be freeze-dried or spray-dried directly, or may be freeze-dried or spray-dried after concentrating under reduced pressure. The resulting extract can be in various forms, such as a liquid extract, solution, powder, concentrate or paste, and can be used in a wide range of forms as necessary.

Moreover, the *acacia* bark extract of the present invention obtained in any of these forms can be used directly as a hypoglycemic composition, or a purified product obtained by purifying the extract as necessary can also be used as a hypoglycemic ingredient.

In the present invention, ingredients contained in bark of the genus *Acacia* are also examples of the *acacia* bark derivatives. Examples of such ingredients are the *acacia* bark polyphenols. The *acacia* bark polyphenols are particularly preferable ingredients since they produce excellent hypoglycemic action.

The *acacia* bark polyphenols of the present invention refer to a type of condensed tannins in the form of polymers in which flavanols having as a basic skeleton flavan-3-ol such as (−)-fisetinidol, (−)-robinetinidol, (+)-catechin and (+)-gallocatechin are linked by C4-C8 or C4-C6 bonds. Here, the molecular weights of such condensed tannins are preferably 300 to 3000 and particularly preferably 500 to 3000. The *acacia* bark polyphenols used in the present invention can be obtained from the powder, etc. of the *acacia* bark by extracting with hot water as previously described.

In addition, examples of commercially available *acacia* bark polyphenols include MIMOSA ME POWDER, MIMOSA MS POWDER, MIMOSA GS POWDER, MIMOSA FS POWDER, MIMOSA WS POWDER, MIMOSA RG POWDER, MIMOSA RN POWDER, MIMOSA DK POWDER, MIMOSA AL POWDER, MIMOSA CR POWDER and GOLDEN MIMOSA POWDER (all registered trademarks) which are manufactured by Mimosa Central Co-operative Ltd., and the like.

Although the composition of the present invention may be the *acacia* bark derivative(s) such as the *acacia* bark, the extract(s) thereof, the purified product(s) thereof or the *acacia* bark polyphenol(s) per se, it may also contain other substance(s) having a hypoglycemic action, such as black vinegar, onion extract or yacon. Yacon and particularly Yacon tea are particularly preferably contained since they produce excellent hypoglycemic actions due to synergistic effects.

Although the composition of the present invention may be the *acacia* bark derivative(s) such as the *acacia* bark, the extract(s) thereof, the purified product(s) thereof or the *acacia* bark polyphenol(s) per se, it may contain vehicles, sweeteners, sour flavorings, thickeners, fragrances, pigments, emulsifiers, and other materials which are ordinarily used in foods, so long as they do not undermine the effects of the present invention.

The composition according to the present invention can be used as a food or an animal feed material, for example, as a health food, a functional food, a health supplement food, a food for specified health use, a beauty food or a nutritional supplement food (supplement) for purposes such as preventing or eliminating a disease accompanied by elevated blood sugar levels such as diabetes or hyperglycemia. For example, these foods or animal feed material may also be in the form of a beverage such as tea or juice; ice cream, jelly, candy, chocolate or chewing gum, etc. In addition, they may also be in the form of liquids, powders, granules, capsules or tablets. Here, animals fed using the animal feed material include all animals requiring the prevention or elimination of diseases accompanied by elevated blood sugar levels, and include pets, livestock or animals bred at zoos, etc.

In addition, the composition according to the present invention can be used as a medicine or a quasi-drug for the prevention, elimination, treatment or the like of a disease accompanied by elevated blood sugar levels such as diabetes or hyperglycemia. These medicine and drug can be administered, for example, orally in the form of tablets, coated tablets, sugar coated pills, hard or soft gelatin capsules, liquids, emulsions or suspensions.

There are no particular limitations on an ingested amount of the composition according to the present invention, and the ingested amount can be suitably selected depending on the dosage form as well as the age, body weight and symptoms of an ingesting person such as a user or patient, or an ingesting animal. For example, it is desired that the ingesting person or ingesting animal orally ingests an amount of the *acacia* bark polyphenol(s) ranging from 0.001 to 1 g, preferably from 0.001 to 0.5 g and more preferably from 0.005 to 0.1 g per 1 kg of body weight per day in terms of the amount of active ingredient, since it produces an excellent hypoglycemic action.

The duration of ingestion can be arbitrarily determined depending on the age and symptoms of the user or patient.

Although the following provides a more detailed explanation of the present invention through examples thereof, the present invention is not limited thereto.

EXAMPLES

Although the following provides a more detailed explanation of the present invention through production examples, test examples and formulation examples thereof, the present invention is not limited thereto. In particular, although the following examples are indicated without making a distinction between the outer bark and inner bark of the *acacia* bark of the present invention, the outer bark can be separated from the inner bark and each can also be used, separately.

In the following production examples, test examples and the like, each *acacia* of the present invention is indicated with numbers shown in parentheses after each scientific name. For example, *acacia* known by the scientific name of *Acacia mearnsii* De Wild. is indicated as *Acacia* No. 1.

Scientific name: *Acacia mearnsii* De Wild. (No. 1), scientific name: *Acacia mangium* Willd. (No. 2), scientific name: *Acacia dealbata* Link (No. 3), scientific name: *Acacia decurrens* Willd. (No. 4), scientific name: *Acacia pycnantha* Benth. (No. 5).

In addition, percentages (%) refer to percent by weight (wt %) unless specifically indicated otherwise.

Production Example 1

*Acacia* Bark Powder

Bark of *Acacia* No. 1 was dried to a moisture content of 20% or less and after pulverizing the dried bark in a hammer mill to a powder having a particle diameter of 1.6 mm or less (the powder passing through a 10 mesh Tyler screen), the powder was further classified with a vibrating screen to obtain a fine powder having a particle diameter of 63 μm or less (passing through a 250 mesh screen).

Fine powders each having a particle diameter of 63 μm or less were similarly obtained by pulverizing bark of the remaining four types of *acacia* namely *Acacia* No. 2 to *Acacia* No. 5. Although there were some differences in the efficiency by which the fine powder passed through the 250 mesh screen depending on the type, all of the target fine powders were able to be obtained.

Production Example 2

*Acacia* Bark Extract

Bark of each *Acacia* No. 1 to 5 of the present invention was dried to a moisture content of 20% or less and after pulverizing the dried bark in a hammer mill to a powder having a particle diameter of 1.6 mm or less, five times the amount of hot water were added to 100 g of the dried pulverized bark followed by extraction for 15 minutes after boiling, and then filtering using a 10 to 20 μm filter. The resulting filtrate was spray-dried in a spray dryer to obtain 40 g of each bark extract.

The bark extracts are hereinafter indicated as *Acacia* Hot Water Extracts Nos. 1 to 5, respectively.

Production Example 3

*Acacia* Bark Extract

*Acacia* bark of the present invention was dried to a moisture content of 20% or less and after pulverizing the dried bark in a hammer mill to a powder having a particle diameter of 1.6 mm or less, five times the amount of ethanol were added to 100 g of the dried pulverized bark followed by extracting for 15 minutes while refluxing after boiling, and then filtering using a 10 to 20 μm filter. After evaporating the ethanol from the resulting filtrate, the concentrate was spray-dried in a closed spray dryer to obtain 40 g of bark extract (to be indicated hereinafter in the manner of *Acacia* Ethanol Extract No. 1).

*Acacia* Ethanol Extracts Nos. 1 to 5 were obtained in the same manner.

Production Example 4

*Acacia* Bark Extract

Three times the amount of ethanol were added to 10 g of the *acacia* hot water extract obtained in Production Example 2 followed by extraction for 15 minutes while refluxing after boiling, and then filtering using a 10 to 20 μm filter. The ethanol was evaporated from the resulting filtrate, water was added thereto, and then freeze-dried to obtain 9 g of extract (to be indicated hereinafter in the manner of *Acacia* Hot Water Extract Ethanol Fraction No. 1).

*Acacia* Hot Water Extract Ethanol fractions Nos. 1 to 5 were obtained in the same manner.

Test Example 1

Blood Sugar Elevation Inhibition Test (1)

1. Test Method

Feed containing 50 of *Acacia* Hot Water Extract No. 1 described in Production Example 2 was fed for 28 days to type II diabetes model mice (C57BLKS/J Iar-+Lepr$^{db}$/+Lepr$^{db}$, males, age 7 weeks). A control group was fed ordinary commercially available feed.

Blood sugar levels, urine glucose levels and plasma insulin levels were measured before the start of dosing and on the day after the final day of dosing. The mice were fasted starting on the day before measurement days. Blood sugar levels and urine glucose levels were measured with the FreeStyle Kissei Meter (C-D036-01014, Kissei Pharmaceutical Co., Ltd.). Insulin levels were measured with the Insulin Mouse T (Shibayagi Co., Ltd.).

Each of the resulting measured values was expressed as the mean±standard error. Testing for the presence of a significant difference from the control group was carried out using the Student's t-test in the presence of a uniform distribution as determined with the F test, and carried out using the Aspin-Welch t-test in the absence of a uniform distribution as determined with the F test. The level of significance was indicated as 5% or 1%.

2. Test Results

The results are shown in the following Tables 1 and 2. None of the mice died or demonstrated abnormalities in general condition.

TABLE 1

Changes in Blood Sugar Levels and Urine Glucose Levels

| | | Blood sugar level (mg/dL) | | Urine glucose level (mg/dL) | |
|---|---|---|---|---|---|
| Dose group | No. of animals | Before dosing | Day 29 after start of dosing | Before dosing | Day 29 after start of dosing |
| Control group | 7 | 288.4 ± 18.0 | 342.1 ± 36.7 | 524.1 ± 33.6 | 464.1 ± 332.0 |
| Acacia Hot Water Extract No. 1 dose group | 7 | 302.4 ± 23.4 | 116.1 ± 13.9** (66.1%) | 407.3 ± 55.2 | 19.4 ± 3.3 (95.8%) |

( ): Rate of decrease (%) versus control group.
**Comparison with control group. It shows P < 0.01.

TABLE 2

Changes in Insulin Levels

| Dose group | No. of animals | Insulin level (ng/mL) Day 29 after start of dosing |
|---|---|---|
| Control group | 7 | 2.7 ± 0.5 |
| Acacia Hot Water Extract No. 1 dose group | 7 | 5.3 ± 0.8* (96.3%) |

( ): Rate of increase (%) versus control group.
*Comparison with control group. It shows P < 0.05.

On the basis of the above results, the *acacia* bark polyphenols were observed to have the effect of inhibiting the elevation of blood sugar levels attributable to diabetes by lowering blood sugar levels as well as diminish symptoms associated with diabetes.

Test Example 2

Blood Sugar Elevation Inhibition Test (2)

1. Test Method

Feed samples respectively containing 0.5, 1.5 and 5.0% of *Acacia* Hot Water Extract No. 1 described in Production Example 2 were fed for 28 days to type II diabetes model mice (BKS.Cg-+Lepr$^{db}$/+Lepr$^{db}$/Jcl, males, age 7 weeks). A control group was fed ordinary commercially available feed.

Each parameter was measured in the same manner as Test Example 1. Furthermore, blood sugar and urine glucose levels were measured before the start of dosing, on day 14 after the start of dosing and on the day after the final day of dosing. In addition, weekly water and food consumption were measured once a week followed by the calculation of the amounts consumed per day. Glycosylated hemoglobin levels were measured on the day after the final day of dosing by immunoinhibition nephelometry.

The resulting measured values were expressed as the mean±standard deviation. Testing for the presence of a significant difference from the control group was carried out using Dunnett's multiple comparison test. The level of significance was indicated as 5% or 1%.

2. Test Results

The results are shown in the following Tables 3 to 7. None of the mice died or demonstrated abnormalities in general condition.

TABLE 3

| | | Food Consumption (g/day) | | | |
|---|---|---|---|---|---|
| | No. of | Measurement weeks | | | |
| Dose group | animals | Week 1 | Week 2 | Week 3 | Week 4 |
| Control group | 7 | 6.1 ± 0.8 | 6.8 ± 0.4 | 5.9 ± 0.4 | 6.0 ± 0.6 |
| Acacia Hot Water Extract No. 1 0.5% dose group | 7 | 6.1 ± 1.3 | 7.4 ± 0.4 | 7.6 ± 0.3** | 7.3 ± 0.1* |
| Acacia Hot Water Extract No. 1 1.5% dose group | 7 | 5.7 ± 0.7 | 6.8 ± 0.9 | 7.0 ± 0.7* | 7.3 ± 0.8* |
| Acacia Hot Water Extract No. 1 5.0% dose group | 7 | 5.8 ± 1.8 | 6.8 ± 1.2 | 7.1 ± 1.3* | 7.3 ± 1.4* |

*Comparison with control group. It shows P < 0.05.
**Comparison with control group. It shows P < 0.01.

TABLE 4

| | | Water Consumption (mg/day) | | | |
|---|---|---|---|---|---|
| | No. of | Measurement weeks | | | |
| Dose group | animals | Week 1 | Week 2 | Week 3 | Week 4 |
| Control group | 7 | 10.9 ± 5.2 | 12.5 ± 6.2 | 12.4 ± 8.2 | 15.2 ± 10.0 |
| Acacia Hot Water Extract No. 1 0.5% dose group | 7 | 9.2 ± 0.6 (15.6%) | 11.2 ± 0.5 (10.4%) | 13.4 ± 1.6 (−8.1%) | 15.5 ± 2.4 (−2.0%) |

TABLE 4-continued

Water Consumption (mg/day)

| Dose group | No. of animals | Measurement weeks | | | |
|---|---|---|---|---|---|
| | | Week 1 | Week 2 | Week 3 | Week 4 |
| Acacia Hot Water Extract No. 1 1.5% dose group | 7 | 7.7 ± 1.6 (29.4%) | 8.9 ± 2.2 (28.8%) | 10.1 ± 1.7 (18.5%) | 11.1 ± 1.4 (27.0%) |
| Acacia Hot Water Extract No. 1 5.0% dose group | 7 | 3.3 ± 0.3** (69.7%) | 4.3 ± 0.5** (65.6%) | 4.6 ± 0.3** (62.9%) | 4.5 ± 0.6** (70.4%) |

( ): Rate of decrease (%) versus control group.
**Comparison with control group. It shows $P < 0.01$.

TABLE 5

Blood Sugar Levels (mg/dL)

| Dose group | No. of animals | Measurement days | | |
|---|---|---|---|---|
| | | Before dosing | Day 14 after start of dosing | Day 29 after start of dosing |
| Control group | 7 | 272.7 ± 22.5 | 293.9 ± 47.9 | 425.4 ± 79.0 |
| Acacia Hot Water Extract No. 1 0.5% dose group | 7 | 273.1 ± 23.4 | 281.4 ± 20.4 (4.3%) | 376.0 ± 67.2 (11.6%) |
| Acacia Hot Water Extract No. 1 1.5% dose group | 7 | 273.3 ± 20.1 | 260.0 ± 46.1 (11.5%) | 333.7 ± 54.8* (21.6%) |
| Acacia Hot Water Extract No. 1 5.0% dose group | 7 | 269.3 ± 16.1 | 248.3 ± 37.6 (15.5%) | 160.3 ± 47.7** (62.3%) |

( ): Rate of decrease (%) versus control group
*Comparison with control group. It shows $P < 0.05$.
**Comparison with control group. It shows $P < 0.01$.

TABLE 6

Urine Glucose Levels (mg/dL)

| Dose group | No. of animals | Measurement days | | |
|---|---|---|---|---|
| | | Before dosing | Day 14 after start of dosing | Day 29 after start of dosing |
| Control group | 7 | 108.1 ± 11.0 | 514.9 ± 381.9 | 651.4 ± 356.3 |
| Acacia Hot Water Extract No. 1 0.5% dose group | 7 | 117.3 ± 29.7 | 140.6 ± 30.4** (72.7%) | 659.0 ± 250.1 (−1.2%) |
| Acacia Hot Water Extract No. 1 1.5% dose group | 7 | 110.6 ± 9.8 | 179.0 ± 129.2* (65.2%) | 527.4 ± 341.0 (19.0%) |
| Acacia Hot Water Extract No. 1 5.0% dose group | 7 | 105.0 ± 1.2 | 110.4 ± 5.9** (78.6%) | 108.0 ± 8.0** (83.4%) |

( ): Rate of decrease (%) versus control group
*Comparison with control group. It shows $P < 0.05$.
**Comparison with control group. It shows $P < 0.01$.

TABLE 7

Insulin and Glycosylated Hemoglobin Levels

| Dose group | No. of animals | Insulin (ng/mL) | Glycosylated hemoglobin (g/dL) |
|---|---|---|---|
| Control group | 7 | 2.6 ± 1.3 | 1.0 ± 0.3 |
| Acacia Hot Water Extract No. 1 0.5% dose group | 7 | 1.5 ± 0.4 (−42.3%) | 1.1 ± 0.1 (−10.0%) |
| Acacia Hot Water Extract No. 1 1.5% dose group | 7 | 3.4 ± 2.0 (30.8%) | 1.0 ± 0.2 (0.0%) |
| Acacia Hot Water Extract No. 1 5.0% dose group | 7 | 4.0 ± 0.9 (53.8%) | 0.5 ± 0.1** (50.0%) |

( ): Rate of increase (%) versus control group for insulin, or rate of decrease (%) versus control group for glycosylated hemoglobin
**Comparison with control group. It shows $P < 0.01$.

According to the above results, since insulin levels were observed to increase while water consumption, blood sugar levels, urine glucose levels and glycosylated hemoglobin levels were observed to decrease dependent on the dose of *Acacia* Hot Water Extract No. 1, symptoms of diabetes such as hypoinsulinemia, polyposia and hyperglycemia were thought to be diminished by the ingestion of the *acacia* bark polyphenols.

Test Example 3

Mutagenicity Test

A mutagenicity test was conducted in compliance with Ministry of Health, Labor and Welfare Notification No. 77 (Sep. 1, 1988). As a result of testing with test substance (*Acacia* Hot Water Extracts Nos. 1 to 5 of Production Example 2) at doses of 156 to 5,000 µg/plate, there were no increases in the numbers of revertant colonies for any of the bacterial strains.

Test Example 4

Micronucleus Test

The ability to induce micronuclei was investigated in vivo in accordance with ordinary methods. *Acacia* Hot Water Extract No. 1 was orally administered twice at 24-hour intervals at daily doses of 2,000, 1,000 and 500 mg/kg to male ICR mice followed by the preparation of micronucleus specimens 24 hours after the final dosing.

*Acacia* Hot Water Extract No. 1 did not demonstrate positive results at any of the dose levels. In addition, there were no constant fluctuations in the simultaneously observed ratio of total polychromatic erythrocytes to total erythrocytes, and inhibition of erythrocyte proliferation was not observed in comparisons with a negative control group.

Test Example 5

Mouse Acute Toxicity Study (Oral Administration)

An acute oral dose toxicity study was conducted using male and female ICR mice in compliance with OECD (Guidelines for the Testing of Chemicals, 401, 1987). As a result, the $LD_{50}$ value of *Acacia* Hot Water Extract No. 1 was 4,468 mg/kg among males and 3,594 mg/kg among females.

Similar results were obtained in the above study for *Acacia* Hot Water Extracts Nos. 2 to 5 of Production Example 2.

Test Example 6

Rat Repeated Dose Toxicity Study (Oral Administration)

A 13-week repeated dose toxicity study was conducted using rats in accordance with ordinary methods. Mixed feed containing 0.5, 1.5 and 5.00 of *Acacia* Hot Water Extract No. 1 was fed to male and female Slc:SD rats.

As a result, none of the rats died or demonstrated abnormalities in examinations, including general condition.

Test Example 7

Human Single Dose Study

Five healthy adult males age 32 to 43 years were given 1500 mg of *Acacia* Hot Water Extract No. 1 (12 tablets of Formulation Example 4 described below). Although general examinations, hematology tests, blood biochemistry tests and urinalyses were performed on the subjects before ingestion, 3 hours after ingestion, 8 hours after ingestion, 24 hours after ingestion and 1 week after ingestion, there were no clinically significant fluctuations in test values. There were also no adverse events attributable to the tablets.

Test Example 8

Human 4-Week Continuous Dosing Study

Twenty-five healthy adult males age 23 to 44 years were given *Acacia* Hot Water Extract No. 1 of Formulation Example 4 described below at 750 mg/day (6 tablets of Formulation Example 4) and 1000 mg/day (8 tablets of Formulation Example 4) for 4 weeks each.

General examinations, hematology tests and urinalyses were performed on the subjects of each group before ingestion, 2 weeks after ingestion, 4 weeks after ingestion and 2 weeks following completion of ingestion. There were no clinically significant fluctuations in test values. There were also no adverse events.

Formulation Example 1

Preparation of Internal Medication

An internal medication having the composition indicated below was prepared using the *acacia* bark Hot Water Extract Ethanol Fraction of Production Example 4.

| | |
|---|---|
| Extract fraction of Production Example 4 | 1.0 (wt %) |
| Lactose | 30.0 |
| Cornstarch | 60.0 |
| Crystalline cellulose | 8.0 |
| Polyvinyl pyrrolidone | 1.0 |
| Total | 100.0 |

Formulation Example 2

Preparation of Pet Food

A pet food having the composition indicated below was prepared using the *acacia* bark Hot Water Extract of Production Example 2.

| | |
|---|---|
| Extract of Production Example 2 | 1.0 (wt %) |
| Oatmeal | 88.0 |
| Starch | 5.0 |
| Salt | 2.5 |
| Whole egg | 3.0 |
| Flavoring | 0.5 |
| Total | 100.0 |

Formulation Example 3

Preparation of Tablets (Confections)

Tablets (confections) having the composition indicated below were prepared using the *acacia* bark Hot Water Extract Ethanol Fraction of Production Example 4.

| | |
|---|---|
| Extract fraction of Production Example 4 | 1.0 (wt %) |
| Citric acid | 1.0 |
| Powdered skim milk | 15.0 |
| Sucrose ester | 1.0 |
| Flavoring | 0.5 |
| Powdered sugar | 20.0 |
| Lactose | 61.5 |
| Total | 100.0 |

Formulation Example 4

Preparation of Tablets

Tablets having the composition indicated below were prepared using *Acacia* Bark Hot Water Extract No. 1 of Production Example 2.

| | |
|---|---|
| *Acacia* Bark Hot Water Extract No. 1 of Production Example 2 | 125 (mg) |
| Sucrose ester | 9 |
| Lactose | 166 |
| Total | 300 |

Industrial Applicability

The hypoglycemic composition of the present invention can be used as a medicine or a quasi-drug; or as a food such as a health food, a health supplement food, a food for specified health use or a nutritional supplement food; or as an animal feed material, for use in eliminating and/or preventing and/or treating diseases accompanied by elevated blood sugar levels.

Examples of the aforementioned diseases accompanied by elevated blood sugar levels include not only diabetes such as type I or type II diabetes and hyperglycemia, but also diseases caused by diabetes or hyperglycemia, including complications such as diabetic hyperlipemia, diabetic osteoporosis, symptoms of weight loss caused by diabetes, symptoms of fluctuations in blood mineral concentrations due to diabetes, diabetic neuropathies such as numbness or pain, cataracts, arteriosclerosis, peripheral circulatory disorders, diabetic gangrene such as gangrene of the lower extremities, diabetic retinopathy or diabetic nephropathy.

In particular, since the composition of the present invention inhibits elevation of blood sugar levels, it is thought to be able to prevent hyperglycemia and even prevent diabetes, thereby making it useful as a health food or a food for specified health use.

The invention claimed is:

1. A method for treating hyperglycemia in a patient in need thereof comprising:
   administering to the patient in need thereof a therapeutically effective amount of a composition consisting of a bark extract of *Acacia* Mearnsii De Wild.; and
   at least one of a food, an animal feed, black vinegar, onion extract, yacon, a pharmaceutical vehicle, a sweetener, a flavoring, a thickener, a fragrance, a pigment, and an emulsifier.

2. The method of claim 1, wherein the bark extract comprises polyphenol(s).

3. The method of claim 2, wherein the polyphenol(s) is a condensed tannin(s) having flavan-3-ol as a basic skeleton and a molecular weight(s) of 500 to 300.

4. The method of claim 2, wherein the composition is orally ingested by the patient at 0.001 to 1 g polyphenol(s) per kg of body weight per day and wherein the patient is an ingesting person or an ingesting animal.

5. The method of claim 1, wherein the vehicle is selected from the group consisting of starch, crystalline cellulose, polyvinylpyrrolidone, sucrose, lactose and powdered skim milk.

6. The method of claim 1, wherein the emulsifier is a sucrose ester.

7. The method of claim 1, wherein the flavoring is citric acid.

8. The method of claim 1, wherein the composition is ingested by the patient to administer the composition.

9. A method for treating hyperglycemia in a patient in need thereof comprising:
   administering to the patient in need thereof a therapeutically effective amount of a composition consisting of a bark extract of *Acacia* Mearnsii De Wild.

10. The method of claim 9, wherein the bark extract comprises polyphenol(s).

11. The method of claim 9, wherein the polyphenol(s) is a condensed tannin(s) having flavan-3-ol as a basic skeleton and a molecular weight(s) of 500 to 300.

12. The method of claim 9, wherein the composition is orally ingested by the patient at 0.001 to 1 g polyphenol(s) per kg of body weight per day and wherein the patient is an ingesting person or an ingesting animal.

* * * * *

UNITED STATES PATENT AND TRADEMARK OFFICE
CERTIFICATE OF CORRECTION

| | | |
|---|---|---|
| PATENT NO. | : 8,128,969 B2 | |
| APPLICATION NO. | : 12/376902 | |
| DATED | : March 6, 2012 | |
| INVENTOR(S) | : Yusho Nakamoto et al. | |

It is certified that error appears in the above-identified patent and that said Letters Patent is hereby corrected as shown below:

Column 6, line 43, change "50 of *Acacia* Hot Water" to --5% of *Acacia* Hot Water--.

Column 11, line 20, change "5.00 of *Acacia* Hot Water" to --5.0% of *Acacia* Hot Water--.

Signed and Sealed this
Twenty-sixth Day of June, 2012

David J. Kappos
*Director of the United States Patent and Trademark Office*